US00RE45976E

(19) United States
(12) Reissued Patent
Tobinick

(10) Patent Number: US RE45,976 E
(45) Date of Reissued Patent: *Apr. 19, 2016

(54) METHODS OF INHIBITING THE ACTION OF TNF FOR NEUROLOGICAL CONDITIONS BY ADMINISTERING ETANERCEPT INTRATHECALLY

(75) Inventor: Edward L. Tobinick, Los Angeles, CA (US)

(73) Assignee: TACT IP, LLC, Highland Beach, FL (US)

( * ) Notice: This patent is subject to a terminal disclaimer.

(21) Appl. No.: 12/344,437

(22) Filed: Dec. 26, 2008

Related U.S. Patent Documents

Reissue of:
(64) Patent No.: 6,015,557
Issued: Jan. 18, 2000
Appl. No.: 09/275,070
Filed: Mar. 23, 1999

U.S. Applications:
(63) Continuation-in-part of application No. 09/256,388, filed on Feb. 24, 1999, now abandoned.

(51) Int. Cl.

| | |
|---|---|
| ***A61K 39/395*** | (2006.01) |
| ***A61K 31/495*** | (2006.01) |
| ***A61K 31/50*** | (2006.01) |
| ***A61K 31/42*** | (2006.01) |
| ***A61K 39/00*** | (2006.01) |

(52) U.S. Cl.
CPC ..... *A61K 39/00* (2013.01)

(58) Field of Classification Search
None
See application file for complete search history.

(56) References Cited

U.S. PATENT DOCUMENTS

| | | | | |
|---|---|---|---|---|
| 5,605,690 | A | 2/1997 | Jacobs et al. | |
| 5,656,272 | A | 8/1997 | Le et al. | |
| 5,698,195 | A | 12/1997 | Le et al. | |
| 5,795,967 | A | 8/1998 | Aggarwal et al. | |
| 5,919,452 | A | 7/1999 | Le et al. | |
| 5,958,409 | A * | 9/1999 | Turk et al. | 424/141.1 |
| 6,015,557 | A * | 1/2000 | Tobinick et al. | 424/134.1 |
| 6,177,077 | B1 * | 1/2001 | Tobinick | 424/134.1 |
| 6,271,196 | B1 * | 8/2001 | O'Brien | 514/2 |
| 6,277,969 | B1 | 8/2001 | Le et al. | |
| 6,284,471 | B1 | 9/2001 | Le et al. | |
| 6,306,820 | B1 * | 10/2001 | Bendele et al. | 514/2 |
| 6,379,666 | B1 * | 4/2002 | Tobinick | 424/134.1 |
| 6,419,934 | B1 * | 7/2002 | Tobinick | 424/400 |
| 6,419,944 | B2 * | 7/2002 | Tobinick | 424/422 |
| 6,423,321 | B2 * | 7/2002 | Tobinick | 424/400 |
| 6,428,787 | B1 * | 8/2002 | Tobinick | 424/134.1 |
| 6,537,549 | B2 * | 3/2003 | Tobinick | 424/134.1 |
| 6,635,250 | B2 | 10/2003 | Olmarker et al. | |
| 6,649,589 | B1 | 11/2003 | Olmarker et al. | |
| 6,835,823 | B2 | 12/2004 | Le et al. | |
| 6,982,089 | B2 * | 1/2006 | Tobinick | 424/400 |
| 6,991,791 | B2 | 1/2006 | Le et al. | |
| 7,115,557 | B2 | 10/2006 | Olmarker | |
| 7,214,658 | B2 * | 5/2007 | Tobinick | 514/2 |
| 7,608,262 | B2 | 10/2009 | Elliott | |
| 7,629,311 | B2 * | 12/2009 | Tobinick | 514/2 |
| 2001/0006948 | A1 * | 7/2001 | Kang et al. | 514/44 |
| 2008/0019964 | A1 | 1/2008 | Olmarker et al. | |
| 2008/0019969 | A1 | 1/2008 | Gorman | |
| 2008/0019970 | A1 | 1/2008 | Gorman | |
| 2008/0019975 | A1 | 1/2008 | Gorman | |
| 2008/0085274 | A1 | 4/2008 | Olmarker et al. | |
| 2008/0213283 | A1 | 9/2008 | Olmarker et al. | |

FOREIGN PATENT DOCUMENTS

| | | |
|---|---|---|
| SE | 9803276 | 9/1998 |
| SE | 9803710 | 10/1998 |
| WO | PCT SE96/1671 | 9/1999 |

OTHER PUBLICATIONS

Dorland's Illustrated Medical Dictionary, Twenty-sixth Edition, edited W. B. Saunders Company, Philadelphia, 1981, p. 970.*
NCI Drug Dictionary Definition of "etanercept" (National Cancer Institute Drug Dictionary obtained on Nov. 12, 2009 from www.cancer.gov/drugdictionary/?CdrID=257809).*
Inoue et al., Nephrol Dial Transplant 10: 207-2082, 1995.*
Merola et al., Neuroendocrinology 64: 393-397, 1996.*
Ignatowski, Society for Neuroscience 24: p. 527, Abstract 212.5, 1998.*
Dorland's Illustrated Medical Dictionary Twenty-sixth Edition, W.B. Saunders Company, Philadelphia, 1981. See pp. 409, 452 and 676.*
Sorbera, Drugs of the Future 23: 951-954, 1998.*

(Continued)

*Primary Examiner* — Phillip Gambel
(74) *Attorney, Agent, or Firm* — Neifeld IP Law

(57) ABSTRACT

A method for inhibiting the action of TNF for treating neurological conditions in a human by administering a TNF antagonist for reducing damage to neuronal tissue or for modulating the immune response affecting neuronal tissue of the human. The TNF antagonist administered is selected from the group consisting of etanercept and infliximab. The TNF antagonist is administered subcutaneously, intravenously, intrathecally, or intramuscularly.
Methotrexate or Leflunomide may be administered concurrently with the TNF antagonist for demyelinating diseases and certain other neurological disorders.

3 Claims, No Drawings

(56) References Cited

OTHER PUBLICATIONS

Abraham, E, et al., *Lenercept (p55 tumor necrosis factor receptor fusion protein) in severe sepsis and early septic shock: A randomized, double-blind, placebo-controlled, multicenter phase III trial with 1,342 patients*. Crit Care Med 2001 vol. 29, No. 3, p. 503-510.

Aisen, P.S. and K.L. Davis, *Inflammatory mechanisms in Alzheimer's disease: implications for therapy*. Am J Psychiatry, 1994. 151(8): p. 1105-13.

Aisen, P.S. and K.L. Davis, *The search for disease-modifying treatment for Alzheimer's disease*. Neurology, 1997. 48(5 Suppl 6): p. S35-41.

Aisen, P.S., K.L. Davis, J.D. Berg, K. Schafer, K. Campbell, R.G. Thomas, M.F. Weiner, M.R. Farlow, M. Sano, M. Grundman, and L.J. Thal, *A randomized controlled trial of prednisone in Alzheimer's disease. Alzheimer's Disease Cooperative Study*. Neurology, 2000. 54(3): p. 588-93.

Al Saieg, N. and M.J. Luzar, *Etanercept induced multiple sclerosis and transverse myelitis*. J Rheumatol, 2006. 33(6): p. 1202-4.

Alvarez, X.A., A. Franco, L. Fernandez-Novoa, and R. Cacabelos, *Blood levels of histamine, IL-1 beta, and TNF-alpha in patients with mild to moderate Alzheimer disease*. Mol Chem Neuropathol, 1996. 29(2-3): p. 237-52.

Anderson, R., *Diodrast studies of the vertebral and cranial venous systems to show their probable role in cerebral metastases*. J Neurosurg, 1951. 8(4): p. 411-22.

Anthony, J.C., J.C.S. Breitner, P.P. Zandi, M.R. Meyer, I. Jurasova, M.C. Norton, and S.V. Stone, *Reduced prevalence of AD in users of NSAIDs and H2 receptor antagonists: the Cache County study*. Neurology, 2000. 54(11): p. 2066-71.

Apkarian, A.V., Y. Sosa, S. Sonty, R.M. Levy, R.N. Harden, T.B. Parrish, and D.R. Gitelman, *Chronic back pain is associated with decreased prefrontal and thalamic gray matter density*. J Neurosci, 2004. 24(46): p. 10410-5.

Banks, W.A., *Are the extracellular* [*correction of extracelluar*] *pathways a conduit for the delivery of therapeutics to the brain*? Curr Pharm Des, 2004. 10(12): p. 1365-70.

Banks, W.A., S.R. Plotkin, and A.J. Kastin, *Permeability of the blood-brain barrier to soluble cytokine receptors*. Neuroimmunomodulation, 1995. 2(3): p. 161-5.

Barger, S.W., D. Horster, K. Furukawa, Y. Goodman, J. Krieglstein, and M.P. Mattson, *Tumor necrosis factors alpha and beta protect neurons against amyloid beta peptide toxicity: evidence for involvement of a kappa B-binding factor and attenuation of peroxide and Ca2+ accumulation*. Proc Natl Acad Sci U S A, 1995. 92(20): p. 9328-32.

Batson, O.V., *The Function of the Vertebral Veins and their role in the spread of metastases*. Annals of Surgery, 1940. 112: p. 138-149.

Batson, O.V., *The Vertebral Vein System, Caldwell Lecture, 1956*. American Journal of Roentgenology, 1957. 78(2).

Bensouda-Grimaldi, L., D. Mulleman, J.P. Valat, and E. Autret-Leca, *Adalimumab-associated multiple sclerosis*. J Rheumatol, 2007. 34(1): p. 239-40; discussion 240.

Bjornberg, F. et al., *Mechanisms Involved in the Process of the p55 and the p75 Tumor Necrosis Factor (TNF) Receptors to Soluble Receptor Forms*. Lymphokine and Cytokine Research, vol. 13, No. 3, 1994, p. 203-211.

Breitner, J.C., *The role of anti-inflammatory drugs in the prevention and treatment of Alzheimer's disease*. Amu Rev Med, 1996. 47: p. 401-11.

Brisby, H., K. Olmarker, K. Larsson, M. Nutu, and B. Rydevik, *Proinflammatory cytokines in cerebrospinal fluid and serum in patients with disc herniation and sciatica*. Eur Spine J, 2002. 11(1): p. 62-6.

Burkovetskaya, M.E., S.G. Levin, and O.V. Godukhin, *Neuroprotective effects of interleukin-10 and tumor necrosis factor-alpha against hypoxia-induced hyperexcitability in hippocampal slice neurons*. Neurosci Lett, 2007. 416(3): p. 236-40.

Byrod, G., K. Olmarker, S. Konno, K. Larsson, K. Takahashi, and B. Rydevik, *A rapid transport route between the epidural space and the intraneural capillaries of the nerve roots*. Spine, 1995. 20(2): p. 138-43.

Byrod, G., B. Rydevik, B.R. Johansson, and K. Olmarker, *Transport of epidurally applied horseradish peroxidase to the endoneurial space of dorsal root ganglia: a light and electron microscopic study*. J Peripher Nerv Syst, 2000. 5(4): p. 218-26.

Cacabelos, R., X.A. Alvarez, A. Franco-Maside, L. Fernandez-Novoa, and J. Caamano, *Serum tumor necrosis factor (TNF) in Alzheimer's disease and multi-infarct dementia*. Methods Find Exp Clin Pharmacol, 1994. 16(1): p. 29-35.

Carlson, N. G., A. Bacchi, S.W. Rogers, and L.C. Gahring, *Nicotine blocks TNF-alpha-mediated neuroprotection to NMDA by an alpha-bungarotoxin-sensitive pathway*. J Neurobiol, 1998. 35(1): p. 29-36.

Chauhan, N.B. and G.J. Siegel, *Intracerebroventricular passive immunization with anti-Abeta antibody in Tg2576*.J Neurosci Res, 2003. 74(1): p. 142-7.

Chauhan, N.B. and G.J. Siegel, *Efficacy of anti-Abeta antibody isotypes used for intracerebroventricular immunization in TgCRND8*. Neurosci Lett, 2005. 375(3): p. 143-7.

Cooper, N.R., R.N. Kalaria, P.L. McGeer, and J. Rogers, *Key issues in Alzheimer's disease inflammation*. Neurobiol Aging, 2000. 21(3): p. 451-453.

Dolga, A.M., I. Granic, T. Blank, H.G. Knaus, J. Spiess, P.G. Luiten, U.L. Eisel, and I.M. Nijholt, *TNF-alpha-mediates neuroprotection against glutamate-induced excitotoxicity via NF-kappaB-dependent up-regulation of K2.2 channels*. J Neurochem, 2008. 107(4): p. 1158-67.

Edsbagge, M., M. Tisell, L. Jacobsson, and C. Wikkelso, *Spinal CSF absorption in healthy individuals*. Am J Physiol Regul Integr Comp Physiol, 2004. 287(6): p. R1450-5.

Edwards, M.M. and S.R. Robinson, TNF alpha affects the expression of GFAP and S100B: implications for Alzheimer's disease. J Neural Transm, 2006. 113(11): p. 1709-15.

Engelborghs, S., M. De Brabander, J. De Cree, R. D'Hooge, H. Geerts, H. Verhaegen, and P.P. De Deyn, *Unchanged levels of interleukins, neopterin, interferon-gamma and tumor necrosis factor-alpha in cerebrospinal fluid of patients with dementia of the Alzheimer type*. Neurochem Int, 1999. 34(6): p. 523-30.

Figiel, I., Pro-inflammatory cytokine TNF-alpha as a neuroprotective agent in the brain. Acta Neurobiol Exp (Wars), 2008. 68(4): p. 526-34.

Fillit, H., W.H. Ding, L. Buee, J. Kalman, L. Altstiel, B. Lawlor, and G. Wolf-Klein, *Elevated circulating tumor necrosis factor levels in Alzheimer's disease*. Neurosci Lett, 1991. 129(2): p. 318-20.

Fontaine, V., S. Mohand-Said, N. Hanoteau, C. Fuchs, K. Pfizenmaier, and U. Eisel, *Neurodegenerative and neuroprotective effects of tumor Necrosis factor (TNF) in retinal ischemia: opposite roles of TNF receptor 1 and TNF receptor 2*. J Neurosci, 2002. 22(7): p. RC216.

Furst, D.E, et al., *Intravenous Human Recombinant Tumor Necrosis Factor Receptor p55-Fc IgG1 Fusion Protein, Ro 45-2081 (Lenercept): Results of a Dose-Finding Study in Rheumatoid Arthritis*. The Journal of Rheumatology, 2003; 30:10, p. 2123-2126.

Gallo, P., M.G. Piccinno, L. Krzalic, and B. Tavolato, *Tumor necrosis factor alpha (TNF alpha) and neurological diseases. Failure in detecting TNF alpha in the cerebrospinal fluid from patients with multiple sclerosis, Aids dementia complex, and brain tumours*. J Neuroimmunol, 1989. 23(1): p. 41-4.

Genevay, S., S. Stingelin, and C. Gabay, *Efficacy of etanercept in the treatment of acute, severe sciatica: a pilot study*. Ann Rheum Dis, 2004. 63(9): p. 1120-3.

Gisolf, J., J.J. van Lieshout, K. van Heusden, F. Pott, W.J. Stok, and J.M. Karemaker, *Human cerebral venous outflow pathway depends on posture and central venous pressure*. J Physiol, 2004. 560(Pt 1): p. 317-27.

Glabinski, A.R., B. Bielecki, J.A. Kawczak, V.K. Tuohy, K. Selmaj, and R.M. Ransohoff, *Treatment with soluble tumor necrosis factor receptor (sTNFR):Fc/p80 fusion protein ameliorates relapsing-remitting experimental autoimmune encephalomyelitis and decreases chemokine expression*. Autoimmunity, 2004. 37(6-7): p. 465-71.

(56) References Cited

OTHER PUBLICATIONS

Goiriz, R., et al., *Flare and change of psoriasis morphology during the course of treatment with tumour necrosis factor blockers*. Clinical and Experimental Dermatology, 32, 176-179, 2006.

Gomez-Gallego, M., J. Meca-Lallana, and A. Femandez-Barreiro, *Multiple sclerosis onset during etanercept treatment*. Eur Neurol, 2008. 59(1-2): p. 91-3.

Goodman, J.C., C.S. Robertson, R.G. Grossman, and R.K. Narayan, *Elevation of tumor necrosis factor in head injury*. J Neuroimmunol, 1990. 30(2-3): p. 213-7.

Griffin, W.S., *Perispinal etanercept: potential as an Alzheimer therapeutic*. J Neuroinflammation, 2008. 5: p. 3.

Groen, R.J., D.F. du Toit, F.M. Phillips, P.V. Hoogland, K. Kuizenga, M.H. Coppes, C.J. Muller, M. Grobbelaar, and J. Mattyssen, *Anatomical and pathological considerations in percutaneous vertebroplasty and kyphoplasty: a reappraisal of the vertebral venous system*. Spine, 2004. 29(13): p. 1465-71.

Hale, K.K, et al., *Multifunctional Regulation of the Biological Effects of TNF-a by the Soluble Type I and Type II TNF Receptors*. Cytokine, vol. 7, 1995; pp. 26-38.

Heldmann, U., P. Thored, J.H. Claasen, A. Arvidsson, Z. Kokaia, and O. Lindvall, *TNF-alpha antibody infusion impairs survival of stroke-generated neuroblasts in adult rat brain*. Exp Neurol, 2005. 196(1): p. 204-8.

Hofman, F.M., D.R. Hinton, K. Johnson, and J.E. Merrill, *Tumor necrosis factor identified in multiple sclerosis brain*. J Exp Med, 1989. 170(2): p. 607-12.

Hulse, R.E., W.G. Swenson, P.E. Kunkler, D.M. White, and R.P. Kraig, *Monomeric IgG is neuroprotective via enhancing microglial recycling endocytosis and TNF-alpha*. J Neurosci, 2008. 28(47): p. 12199-211.

Ibukuro, K., H. Fukuda, K. Mori, and Y. Inoue, *Topographic anatomy of the vertebral venous system in the thoracic inlet*. AJR Am J Roentgenol, 2001. 176(4): p. 1059-65.

Igarashi, A., S. Kikuchi, S. Konno, and K. Olmarker, *Inflammatory cytokines released from the facet joint tissue in degenerative lumbar spinal disorders*. Spine, 2004. 29(19): p. 2091-5.

Klegeris, A., D.G. Walker, and P.L. McGeer, *Interaction of Alzheimer beta-amyloid peptide with the human monocytic cell line THP-1 results in a protein kinase C-dependent secretion of tumor necrosis factor-alpha*. Brain Res, 1997. 747(1): p. 114-21.

Klinkert, W.E., K. Kojima, W. Lesslauer, W. Rinner, H. Lassmann, and H. Wekerle, *TNF-alpha receptor fusion protein prevents experimental autoimmune encephalomyelitis and demyelination in Lewis rats: an overview*. J Neuroimmunol, 1997. 72(2): p. 163-8.

Knoblach, S.M., L. Fan, and A.I. Faden, *Early neuronal expression of tumor necrosis factor-alpha after experimental brain injury contributes to neurological impairment*. J Neuroimmunol, 1999. 95(1-2): p. 115-25.

Koopman, W.J, et al. *Rheumatoid Arthritis: Anticytokine Therapies on the Horizon*, vol. 128, Issue 3; pp. 231-233, Feb. 1998.

Larsson, K., B. Rydevik, and K. Olmarker, *Disc related cytokines inhibit axonal outgrowth from dorsal root ganglion cells in vitro*. Spine, 2005. 30(6): p. 621-4.

Laws, S.M., R. Pemeczky, S. Wagenpfeil, U. Muller, H. Forstl, R.N. Martins, A. Kurz, and M. Riemenschneider, *TNF polymorphisms in Alzheimer disease and functional implications on CSF beta-amyloid levels*. Hum Mutat, 2005. 26(1): p. 29-35.

Lirk, P., C. Kolbitsch, G. Putz, J. Colvin, H.P. Colvin, I. Lorenz, C. Keller, L. Kirchmair, J. Rieder, and B. Moriggl, *Cervical and high thoracic ligamentum flavum frequently fails to fuse in the midline*. Anesthesiology, 2003. 99(6): p. 1387-90.

Lirk, P., B. Moriggl, J. Colvin, C. Keller, L. Kirchmair, J. Rieder, and C. Kolbitsch, *The incidence of lumbar ligamentum flavum midline gaps*. Anesth Analg, 2004. 98(4): p. 1178-80, table of contents.

Maness, L.M., W.A. Banks, J.E. Zadina, and A.J. Kastin, *Selective transport of blood-borne interleukin-1 alpha into the posterior division of the septum of the mouse brain*. Brain Res, 1995. 700(1-2): p. 83-8.

Marchetti, L., M. Klein, K. Schlett, K. Pfizenmaier, and U.L. Eisel, *Tumor necrosis factor (TNF)-mediated neuroprotection against glutamate-induced excitotoxicity is enhanced by N-methyl-D-aspartate receptor activation. Essential role of a TNF receptor 2-mediated phosphatidylinositol 3-kinasedependent NF-kappa B pathway*. J Biol Chem, 2004. 279(31): p. 32869-81.

Masseguin, C., L. Mani-Ponset, S. Herbute, A. Tixier-Vidal, and J. Gabrion, *Persistence of tight junctions and changes in apical structures and protein expression in choroid plexus epithelium of rats after short-term head-down tilt*. J Neurocytol, 2001. 30(5): p. 365-77.

Mastroianni, C.M., F. Paoletti, C. Valenti, V. Vullo, E. Jirillo, and S. Delia, *Tumour necrosis factor (TNF-alpha) and neurological disorders in HIV infection*. J Neurol Neurosurg Psychiatry, 1992. 55(3): p. 219-21.

Mattson, M.P., S.W. Barger, K. Furukawa, A.J. Bruce, T. Wyss-Coray, R.J. Mark, and L. Mucke, *Cellular signaling roles of TGF beta, TNF alpha and beta APP in brain injury responses and Alzheimer's disease*. Brain Res Brain Res Rev, 1997. 23(1-2): p. 47-61.

McGeer, P.L., M. Schulzer, and E.G. McGeer, *Arthritis and anti-inflammatory agents as possible protective factors for Alzheimer's disease: a review of 17 epidemiologic studies*. Neurology, 1996. 47(2): p. 425-32.

Medeiros, R., R.D. Prediger, G.F. Passos, P. Pandolfo, F.S. Duarte, J.L. Franco, A.L. Dafre, G. Di Giunta, C.P. Figueiredo, R.N. Takahashi, M.M. Campos, and J.B. Calixto, *Connecting TNF-alpha signaling pathways to iNOS expression in a mouse model of Alzheimer's disease: relevance for the behavioral and synaptic deficits induced by amyloid beta protein*. J Neurosci, 2007. 27(20): p. 5394-404.

Mohan, N., E.T. Edwards, T.R. Cupps, P.J. Oliverio, G. Sandberg, H. Crayton, J.R. Richert, and J.N. Siegel, *Demyelination occurring during antitumor necrosis factor alpha therapy for inflammatory arthritides*. Arthritis Rheum, 2001. 44(12): p. 2862-9.

Mohler, K.M., D.S. Torrance, C.A. Smith, R.G. Goodwin, K.E. Stremler, V.P. Fung, H. Madani, and M.B. Widmer, *Soluble tumor necrosis factor (TNF) receptors are effective therapeutic agents in lethal endotoxemia and function simultaneously as both TNF carriers and TNF antagonists*. J Immunol, 1993. 151(3): p. 1548-61.

Murata, Y., U. Nannmark, B. Rydevik, K. Takahashi, and K. Olmarker, *Nucleus pulposus-induced apoptosis in dorsal root ganglion following experimental disc herniation in rats*. Spine, 2006. 31(4): p. 382-90.

Murata, Y., U. Nannmark, B. Rydevik, K. Takahashi, and K. Olmarker, *The role of tumor necrosis factor-alpha in apoptosis of dorsal root ganglion cells induced by herniated nucleus pulposus in rats*. Spine, 2008. 33(2): p. 155-62.

Murata, Y., K. Olmarker, K. Larsson, K. Takahashi, and B. Rydevik, *Production of tumor necrosis factor-alpha from porcine nucleus pulposus cells at various time points in cell culture under conditions of nutritional deficiency*. Cytokine, 2006. 34(3-4): p. 206-11.

Murata, Y., A. Onda, B. Rydevik, I. Takahashi, K. Takahashi, and K. Olmarker, *Changes in pain behavior and histologic changes caused by application of tumor necrosis factor-alpha to the dorsal root ganglion in rats*. Spine, 2006. 31(5): p. 530-5.

Murata, Y., A. Onda, B. Rydevik, K. Takahashi, and K. Olmarker, *Selective inhibition of tumor necrosis factor-alpha prevents nucleus pulposus-induced histologic changes in the dorsal root ganglion*. Spine, 2004. 29(22): p. 2477- 84.

Murata, Y., A. Onda, B. Rydevik, K. Takahashi, and K. Olmarker, *Distribution and appearance of tumor necrosis factor-alpha in the dorsal root ganglion exposed to experimental disc herniation in rats*. Spine, 2004. 29(20): p. 2235-41.

Nawashiro, H., D. Martin, and J.M. Hallenbeck, *Neuroprotective effects of TNF binding protein in focal cerebral ischemia*. Brain Res, 1997. 778(2): p. 265-71.

Nedjai, B. et al., *Proinflammatory Action of the Antiinflammatory Drug Infliximab in Tumor Necrosis Factor Receptor—Associated Periodic Syndrome*. Arthritis & Rheumatism, vol. 60, No. 2, 2009, pp. 619-625.

Olmarker, K., *Radicular pain—recent pathophysiologic concepts and therapeutic implications*. Schmerz, 2001. 15(6): p. 425-9.

(56) References Cited

OTHER PUBLICATIONS

Olmarker, K., G. Byrod, M. Cornefjord, C. Nordborg, and B. Rydevik, *Effects of methylprednisolone on nucleus pulposus-induced nerve root injury*. Spine, 1994. 19(16): p. 1803-8.
Olmarker, K. And K. Larsson, *Tumor necrosis factor alpha and nucleus-pulposus-induced nerve root injury*. Spine, 1998. 23(23): p. 2538-44.
Olmarker, K., M. Nutu, and R. Storkson, *Changes in spontaneous behavior in rats exposed to experimental disc herniation are blocked by selective TNF-alpha inhibition*. Spine, 2003. 28(15): p. 1635-41; discussion 1642.
Olmarker, K. and B. Rydevik, *Selective inhibition of tumor necrosis factor-alpha prevents nucleus pulposus-induced thrombus formation, intraneural edema, and reduction of nerve conduction velocity: possible implications for future pharmacologic treatment strategies of sciatica*. Spine, 2001. 26(8): p. 863-9.
Onda, A., Y. Murata, B. Rydevik, K. Larsson, S. Kikuchi, and K. Olmarker, Infliximab attenuates immunoreactivity of brain-derived neurotrophic factor in a rat model of herniated nucleus pulposus. Spine, 2004. 29(17): p. 1857-61.
Pardridge, W.M., *The blood-brain barrier: bottleneck in brain drug development*. NeuroRx, 2005. 2(1): p. 3-14.
Perry, R.T., J.S. Collins, H. Wiener, R. Acton, and R.C. Go, *The role of TNF and its receptors in Alzheimer's disease*. Neurobiol Aging, 2001. 22(6): p. 873-83.
Pickering, M., D. Cumiskey, and J.J. O'Connor, *Actions of TNF-alpha on glutamatergic synaptic transmission in the central nervous system*. Exp Physiol, 2005. 90(5): p. 663-70.
Ramos, E.M., M.T. Lin, E.B. Larson, I. Maezawa, L.H. Tseng, K.L. Edwards, G.D. Schellenberg, J.A. Hansen, W.A. Kukull, and L.W. Jin, *Tumor necrosis factor alpha and interleukin 10 promoter region polymorphisms and risk of late-onset Alzheimer disease*. Arch Neurol, 2006. 63(8): p. 1165-9.
Rutgeerts, P., L. Lemmens, G. Van Assche, M. Noman, I. Borghini-Fuhrer, and R. Goedkoop, *Treatment of active Crohn's disease with onercept (recombinant human soluble p55 tumour necrosis factor receptor): results of a randomized, open-label, pilot study*. Aliment Pharmacol Ther, 2003. 17(2): p. 185-92.
Saha, R.N., X. Liu, and K. Pahan, *Up-regulation of BDNF in astrocytes by TNF-alpha: a case for the neuroprotective role of cytokine*. J Neuroimmune Pharmacol, 2006. 1(3): p. 212-22.
San Millan Ruiz, D., P. Gailloud, D.A. Rufenacht, J. Delavelle, F. Henry, and J.H. Fasel, *The craniocervical venous system in relation to cerebral venous drainage*. AJNR Am J Neuroradiol, 2002. 23(9): p. 1500-8.
Scallon, B.J. et al., *Functional comparisons of different tumor necrosis factor receptor/IgG fusion proteins*. Cytokine, vol. 7, No. 8 Nov. 1995: pp. 759-770.
Scallon, B., Cai, A. et al., *Binding and Functional Comparisons of Two Types of Tumor Necrosis Factor Antagonists*. Pharmacol Exp Ther, 2002. 301(2): p. 418-26.
Sharma, H.S., T. Winkler, E. Stalberg, T. Gordh, P. Alm, and J. Westman, *Topical application of TNF-alpha antiserum attenuates spinal cord trauma induced edema formation, microvascular permeability disturbances and cell injury in the rat*. Acta Neurochir Suppl, 2003. 86: p. 407-13.
Sheng, J.G., S.H. Bora, G. Xu, D.R. Borchelt, D.L. Price, and V.E. Koliatsos, *Lipopolysaccharide-induced-neuroinflammation increases intracellular accumulation of amyloid precursor protein and amyloid beta peptide in APPswe transgenic mice*. Neurobiol Dis, 2003. 14(1): p. 133-45.
Shinpo, K., S. Kikuchi, F. Moriwaka, and K. Tashiro, *Protective effects of the TNF-ceramide pathway against glutamate neurotoxicity on cultured mesencephalic neurons*. Brain Res, 1999. 819(1-2): p. 170-3.
Shohami, E., R. Gallily, R. Mechoulam, R. Bass, and T. Ben-Hur, *Cytokine production in the brain following closed head injury: dexanabinol (HU-211) is a novel TNF-alpha inhibitor and an effective neuroprotectant*. J Neuroimmunol, 1997. 72(2): p. 169-77.
Shubayev, V.I. and R.R. Myers, *Upregulation and interaction of TNFalpha and gelatinases A and B in painful peripheral nerve injury*. Brain Res, 2000. 855(1): p. 83-9.
Shubayev, V.I. and R.R. Myers, *Axonal transport of TNF-alpha in painful neuropathy: distribution of ligand tracer and TNF receptors*. J Neuroimmunol, 2001. 114(1-2): p. 48-56.
Shubayev, V.I. and R.R. Myers, *Anterograde TNF alpha transport from rat dorsal root ganglion to spinal cord and injured sciatic nerve*. Neurosci Lett, 2002. 320(1-2): p. 99-101.
Shubayev, V.I. and R.R. Myers, *Endoneurial remodeling by TNFalph- and TNFalpha-releasing proteases. A spatial and temporal co-localization study in painful neuropathy*. J Peripher Nery Syst, 2002. 7(1): p. 28-36.
Sicotte, N. L. and R.R. Voskuhl, *Onset of multiple sclerosis associated with anti-TNF therapy*. Neurology, 2001. 57(10): p. 1885-8.
Sjogren, M., S. Folkesson, K. Blennow, and E. Tarkowski, *Increased intrathecal inflammatory activity in frontotemporal dementia: pathophysiological implications*. J Neurol Neurosurg Psychiatry, 2004. 75(8): p. 1107-11.
Sommer, C., M. Schafers, M. Marziniak, and K.V. Toyka, *Etanercept reduces hyperalgesia in experimental painful neuropathy*. J Peripher Nery Syst, 2001. 6(2): p. 67-72.
Spuler, S., T. Yousry, A. Scheller, R. Voltz, E. Holler, M. Hartmann, M. Wick, and R. Hohlfeld, *Multiple sclerosis: prospective analysis of TNF-alpha and 55 kDa TNF receptor in CSF and serum in correlation with clinical and MRI activity*. J Neuroimmunol, 1996. 66(1-2): p. 57-64.
Suzuki, T., I. Hide, K. Ido, S. Kohsaka, K. Inoue, and Y. Nakata, *Production and release of neuroprotective tumor necrosis factor by P2X7 receptor-activated microglia*. J Neurosci, 2004. 24(1): p. 1-7.
Tariot, P.N. and H.J. Federoff, *Current treatment for Alzheimer disease and future prospects*. Alzheimer Dis Assoc Disord, 2003. 17 Suppl 4: p. S105-13.
Tarkowski, E., *Cytokines in dementias*. Curr Drug Targets Inflamm Allergy, 2002. 1(2): p. 193-200.
Tarkowski, E., N. Andreasen, A. Tarkowski, and K. Blennow, *Intrathecal inflammation precedes development of Alzheimer's disease*. J Neurol Neurosurg Psychiatry, 2003. 74(9): p. 1200-5.
Tarkowski, E., K. Blennow, A. Wallin, and A. Tarkowski, *Intracerebral production of tumor necrosis factor-alpha, a local neuroprotective agent, in Alzheimer disease and vascular dementia*. J Clin Immunol, 1999. 19(4): p. 223-30.
Tarkowski, E., A.M. Liljeroth, L. Minthon, A. Tarkowski, A. Wallin, and K. Blennow, *Cerebral pattern of pro- and anti-inflammatory cytokines in dementias*. Brain Res Bull, 2003. 61(3): p. 255-60.
Tartaglia, L.A., R.F. Weber, I.S. Figari, C. Reynolds, M.A. Palladino, Jr., and D.V. Goeddel, *The two different receptors for tumor necrosis factor mediate distinct cellular responses*. Proc Natl Acad Sci U S A, 1991. 88(20): p. 9292-6.
Tedde, A., A.L. Putignano, B. Nacmias, S. Bagnoli, E. Cellini, and S. Sorbi, *Lack of association between TNF-alpha polymorphisms and Alzheimer's disease in an Italian cohort*. Neurosci Lett, 2008.
Terrado, J., D. Monnier, D. Perrelet, D. Vesin, S. Jemelin, W.A. Buurman, L. Mattenberger, B. King, A.C. Kato, and I. Garcia, *Soluble TNF receptors partially protect injured motoneurons in the postnatal CNS*. Eur J Neurosci, 2000. 12(9): p. 3443-7.
*TNF neutralization in MS: results of a randomized, placebo-controlled multicenter study. The Lenercept Multiple Sclerosis Study Group and The University of British Columbia MS/MRI Analysis Group*. Neurology, 1999. 53(3): p. 457-65.
Tobinick, E., *TNF-alpha inhibition for potential therapeutic modulation of SARS coronavirus infection*. Curr Med Res Opin, 2004. 20(1): p. 39-40.
Tobinick, E., *Spinal delivery of p38: TNF-alpha inhibitors*. PLoS Med, 2006. 3(11): p. e511.
Tobinick, E., *Perispinal etanercept for treatment of Alzheimer's disease*. Curr Alzheimer Res, 2007. 4(5): p. 550-2.
Tobinick, E., *Perispinal etanercept for neuroinflammatory disorders*. Drug Discov Today, 2008.
Tobinick, E., *Perispinal etanercept produces rapid improvement in primary progressive aphasia: identification of a novel, rapidly reversible TNF-mediated pathophysiologic mechanism*. Medscape J Med, 2008. 10(6): p. 135.

(56) References Cited

OTHER PUBLICATIONS

Tobinick, E. and S. Davoodifar, *Efficacy of etanercept delivered by perispinal administration for chronic back and/or neck disc-related pain: a study of clinical observations in 143 patients*. Curr Med Res Opin, 2004. 20(7): p. 1075-85.
Tobinick, E., H. Gross, A. Weinberger, and H. Cohen, *TNF-alpha modulation for treatment of Alzheimer's disease: a 6-month pilot study*. MedGenMed, 2006. 8(2): p. 25.
Tobinick, E. and C.P. Vega, *The cerebrospinal venous system: anatomy, physiology, and clinical implications*. MedGenMed, 2006. 8(1): p. 53.
Tobinick, E.L., *Targeted etanercept for treatment-refractory pain due to bone metastasis: two case reports*. Clin Ther, 2003. 25(8): p. 2279-88.
Tobinick, E.L., *Targeted etanercept for discogenic neck pain: uncontrolled, open-label results in two adults*. Clin Ther, 2003. 25(4): p. 1211-8.
Tobinick, E.L., *Re: Inflammatory markers and the risk of Alzheimer disease: the Framingham Study*. Neurology, 2008. 70(14): p. 1222-3; author reply 1223.
Tobinick, E.L., *A critique of intradiscal administration for treatment of radiculopathy*. Anesthesiology, 2008. 108(2): p. 334; author reply 335.
Tobinick, E.L. and S. Britschgi-Davoodifar, *Perispinal TNF-alpha inhibition for discogenic pain*. Swiss Med Wkly, 2003. 133(11-12): p. 170-7.
Tobinick, E.L. and H. Gross, *Rapid improvement in verbal fluency and aphasia following perispinal etanercept in Alzheimer's disease*. BMC Neurol, 2008. 8: p. 27.
Tobinick, E.L. and H. Gross, *Rapid cognitive improvement in Alzheimer's disease following perispinal etanercept administration*. J Neuroinflammation, 2008. 5: p. 2.
Tracey, D. et al. *Tumor necrosis factor antagonist mechanisms of action: A comprehensive review*. Pharmacology & Therapeutics 117 (2008) pp. 244-279.
Tracey, K.J. and Cerami, A. *Tumor necrosis factor: An updated review of its biology*. Critical Care Medicine, vol. 21, No. 10, pp. S415-S422, 1993.
Turrin, N.P. and S. Rivest, *Tumor necrosis factor alpha but not interleukin 1 beta mediates neuroprotection in response to acute nitric oxide excitotoxicity*. J Neurosci, 2006. 26(1): p. 143-51.
van Oosten, B.W., F. Barkhof, L. Truyen, J.B. Boringa, F.W. Bertelsmann, B.M. von Blomberg, J.N. Woody, H.P. Hartung, and C.H. Polman, *Increased MRI activity and immune activation in two multiple sclerosis patients treated with the monoclonal anti-tumor necrosis factor antibody cA2*. Neurology, 1996. 47(6): p. 1531-4.
Virna, S., M. Deckert, S. Lutjen, S. Soltek, K.E. Foulds, H. Shen, H. Korner, J.D. Sedgwick, and D. Schluter, *TNF is important for pathogen control and limits brain damage in murine cerebral listeriosis*. J Immunol, 2006. 177(6): p. 3972-82.
Wagner, R. and R.R. Myers, *Endoneurial injection of TNF-alpha produces neuropathic pain behaviors*. Neuroreport, 1996. 7(18): p. 2897-901.
Wen, T.S., D.C. Randall, and J.F. Zolman, *Protein accumulation in cerebrospinal fluid during −90 degrees head-down tilt in rabbit*. J Appl Physiol, 1994. 77(3): p. 1081-6.
Wiendl, H. and R. Hohlfeld, *Therapeutic approaches in multiple sclerosis: lessons from failed and interrupted treatment trials*. BioDrugs, 2002. 16(3): p. 183-200.
Wilson, C.J., C.E. Finch, and H.J. Cohen, *Cytokines and cognition—the case for a head-to-toe inflammatory paradigm*. J Am Geriatr Soc, 2002. 50(12): p. 2041-56.
Carlson, N. G, Whitney A. Wieggel,† Jian Chen,† Annalisa Bacchi,\ Scott W. Rogers, and Lorise C. Gahring, Inflammatory Cytokines IL-1a, IL-1b, IL-6, and TNF-a Impart Neuroprotection to an Excitotoxin Through Distinct Pathways. The Journal of Immunology, 1999, 163: 3963-3968.
U.S. Appl. No. 11/986,423, filed Nov. 21, 2007.
U.S. Appl. No. 11/601,799, filed Nov. 17, 2006.
U.S. Appl. No. 11/262,528, filed Oct. 28, 2005.
U.S. Appl. No. 11/016,047, filed Dec. 18, 2004.
U.S. Appl. No. 10/393,540, filed Mar. 21, 2003.
U.S. Appl. No. 10/340,890, filed Jan. 13, 2003.
U.S. Appl. No. 10/269,745, filed Oct. 9, 2002.
U.S. Appl. No. 10/236,097, filed Sep. 6, 2002.
U.S. Appl. No. 10/152,477, filed May 23, 2002.
U.S. Appl. No. 10/152,476, filed May 23, 2002.
U.S. Appl. No. 09/841,844, filed Apr. 25, 2001.
U.S. Appl. No. 09/826,976, filed Apr. 5, 2001.
Looseley A. Corning and Cocaine: the Advent of Spinal Anaesthesia: *Grand Rounds in Exp-Med*, 9, L1-L4 (2009), DOI:10 ,1102/1470-5206.2009.L001.
Calthorpe N. Development of the Cutting Spinal Needle TipThe history of spinal needles: getting to the point, *Anaesthesia*, 59, 1231-1241 (2004).
Gerancher JC. Combined Spinal-Epidural Techniques in Obstetrics. *Techniques in Regional Anesthesia and Pain Management*, 2(4), 179-187 (1998).
Cousins MJ, Bridenbaugh PO. *Spinal Anesthesia, Chapier 1* (p. 11: *History of Neural Blockade and Pain Management,*) in Neural Bllockade in Clinical Anesthesia and Management of Pain (Lippencott-Raven, New York, 1998).
Harger JR, Christofferson EA, Stokes AJ. Peridural Anesthesia: A Consideration of 1000 Cases. *American Journal qf Surgery*, 52(1), 24-31 (1941).
Corning JL. A Further Contribution on Local Medication of the Spinal Cord, with Cases. *Transactions of the Medical Society of the State of New York*, 260-269 (1888).
Corning JL. *Spinal Anaesthesia and Local Medication of the Cord*, Chapter 11 in Local Anaesthesia in General Medicine and Surgery (D. Appleton and Company; New York, 1886).
Pardridge, W.M, *The Blood-Brain Barrier: Bottleneck in Brain Drug Development*, The Journal of the American Society for Experimental NeuroTherapeuties vol. 2, Jan. 3-14, 2005.
Duale et al., *Epidural versus intrathecal morphine for postoperative analgesia after Caesarean section*, British Journal of Anesthesia 91 (5): 690-4 (2003)
Gourlay et al., *Cephalad Migration of Morphine in CSF Following Lumbar Epidural Administration in Patients with Cancer Pain*, Pain, 23 (1985) 317-326.
Nordberg et al., Anesthesiology, 58, 545-551, 1983; Max et al , Clin Pharmacol Ther 38:631-641, 1985.
Max, et al., *Epidural and intrathecal opiates: Cerebrospinal fluid and plasma profiles in patients with chronic cancer pain* Clin Pharmacol Ther 38:631-641, 1985.
Plancarte et al., Currrent Opinion in Anesthesiology 1994, 7:444-447.

* cited by examiner

METHODS OF INHIBITING THE ACTION OF TNF FOR NEUROLOGICAL CONDITIONS BY ADMINISTERING ETANERCEPT INTRATHECALLY

Matter enclosed in heavy brackets [ ] appears in the original patent but forms no part of this reissue specification; matter printed in italics indicates the additions made by reissue; a claim printed with strikethrough indicates that the claim was canceled, disclaimed, or held invalid by a prior post-patent action or proceeding.

RELATED APPLICATION

This is a [continuation-in-part of application Ser. No. 09/256,388, filed on Feb. 24, 1999, now abandoned.] *Reissue of U.S. Pat. No. 6,015,557, which matured from application Ser. No. 09/275,070, filed Mar. 23, 1999, which is a continuation-in-part of application Ser. No. 09/256,388, filed Feb. 24, 1999* (*abandoned*).

FIELD OF THE INVENTION

The present invention relates to tumor necrosis factor (TNF) antagonists or TNF blockers for the treatment of neurological disorders, trauma, injuries or compression; or demyelinating neurological disorders, including multiple sclerosis. More particularly, the TNF antagonists or TNF blockers, with or without the concurrent administration of methotrexate or Leflunomide, are used in a new treatment of these disorders by inhibiting the action of TNF in the cells of the human body. The use of these TNF antagonists or TNF blockers with methotrexate or Leflunomide results in the amelioration of these neurological conditions.

BACKGROUND OF THE INVENTION

Neurological disorders due to demyelinating disease (e.g. multiple sclerosis), immune disease, inflammation, trauma, or compression, occur in different clinical forms depending upon the anatomic site and the cause and natural history of the physiological problem. Common to all of these disorders is the fact that they can cause permanent neurological damage, that damage can occur rapidly and be irreversible, and that current treatment of these conditions is unsatisfactory, often requiring surgery and/or the use of pharmacologic agents, which are often not completely successful.

These neurological conditions include acute spinal cord trauma, spinal cord compression, spinal cord hematoma, cord contusion (these cases are usually traumatic, such as motorcycle accidents or sports injuries); nerve compression, the most common condition being a herniated disc causing sciatic nerve compression, neuropathy, and pain; but also including cervical disc herniation, causing nerve compression in the neck; carnal tunnel syndrome (non-RA); acute or chronic spinal cord compression from cancer (this is usually due to metastases to the spine, such as from prostate, breast or lung cancer); autoimmune disease of the nervous system; and demyelinating diseases, the most common condition being multiple sclerosis.

Steroid drugs such as cortisone that are used to treat the aforementioned neurological problems and conditions are particularly hazardous because they are used either at high dosage, with a corresponding increasing risk of side effects, or because they are used chronically, also increasing their adverse effects. Lastly, steroids are only partially effective or completely ineffective.

There remains a need for a new pharmacologic treatment of these aforementioned physiological problems of the nervous system associated with autoimmune disease, demyelinating diseases, trauma, injuries and compression with the pharmacological use of TNF antagonists or TNF blockers, which are greatly beneficial for the large number of patients whom these conditions affect. Two new drugs which are powerful TNF blockers are etanercept and infliximab. Etanercept or infliximab may be used for the immediate, short term and long term (acute and chronic) blockade of TNF in order to minimize neurologic damage mediated by TNF dependent processes occurring in the aforementioned neurological disorders. The use of these TNF antagonists or TNF blockers would result in the amelioration of these physiological neurological problems. Concurrent administration of methotrexate or Leflunomide with either etanercept or infliximab is the preferred treatment for demyelinating diseases and certain other neurological disorders.

DESCRIPTION OF THE PRIOR ART

Pharmacologic chemical substances, compounds and agents which are used for the treatment of neurological disorders, trauma, injuries and compression having various organic structures and metabolic functions have been disclosed in the prior art. For example, U.S. Pat. Nos. 5,756,482 and 5,574,022 to ROBERTS et al disclose methods of attenuating physical damage to the nervous system and to the spinal cord after injury using steroid hormones or steroid precursors such as pregnenolone, and pregnenolone sulfate in conjunction with a non-steroidal anti-inflammatory substance such as indomethacin. These prior art patents do not teach the use of a TNF antagonist or TNF blocker for the suppression and inhibition of the action of TNF in the human body to treat neurological disease, trauma, injury or compression, or autoimmune neurologic disease as in the present invention.

U.S. Pat. No. 5,605,690 to JACOBS discloses a method for treating TNF-dependent inflammatory diseases such as arthritis by administering a TNF antagonist, such as soluble human TNFR (a sequence of amino acids), to a human. This prior art patent does not teach the use of a TNF antagonist or TNF blocker for the suppression and inhibition of the action of TNF in the human body to treat neurological disease, trauma, injury or compression, or demyelinating neurologic disease, as in the present invention.

U.S. Pat. No. 5,656,272 to LE et al discloses methods of treating TNF-alpha-mediated Crohn's disease using chimeric anti-TNF antibodies. This prior art patent does not teach the use of a TNF antagonist or TNF blocker for the suppression and inhibition of the action of TNF in the human body to treat neurological trauma, injury or compression, or autoimmune neurologic disease, as in the present invention.

U.S. Pat. No. 5,650,396 discloses a method of treating multiple sclerosis (MS) by blocking and inhibiting the action of TNF in a patient. This prior art patent does not teach the use of the TNF antagonist as in the present invention.

None of the prior art patents disclose or teach the use of the TNF antagonist or TNF blocker of the present invention with the concurrent administration of methotrexate or Leflunomide for suppression and inhibition of the action of TNF in a human to treat neurological disease, trauma, injury or compression, or demyelinating neurologic disease, in which the TNF antagonist gives the patient a better opportunity to heal, slows disease progression, prevents neurological damage, or otherwise improves the patient's health.

Accordingly, it is an object of the present invention to provide a TNF antagonist, with or without the concurrent administration of methotrexate or Leflunomide, for a new pharmacologic treatment of neurological disorders, trauma, injuries and compression affecting the nervous system of the human body, or demyelinating neurologic disease, such that the use of these TNF antagonists will result in the amelioration of these neurological conditions.

Another object of the present invention is to provide a TNF antagonist, with or without the concurrent administration of methotrexate or Leflunomide, for providing suppression and inhibition of the action of TNF in a human to treat neurological injury, trauma or compression, or demyelinating neurologic disease.

Another object of the present invention is to provide a TNF antagonist, with or without the concurrent administration of methotrexate or Leflunomide, that reduces inflammation to the patient by inhibiting the action of TNF in the human body for the immediate, short term (acute conditions) and long term (chronic conditions), such that this reduction in inflammation will produce clinical improvement in the patient and will give the patient a better opportunity to heal, slows disease progression, prevents neurological damage, or otherwise improves the patient's health.

Another object of the present invention is to provide a TNF antagonist, with or without the concurrent administration of methotrexate or Leflunomide, that can offer acute and chronic treatment regimens for neurological conditions caused by neurological trauma, compression, injury and/or disease, such conditions including acute spinal cord injury, herniated nucleus pulposus (herniated disc), spinal cord compression due to metastatic cancer, carpal tunnel syndrome, pituitary adenoma, primary or metastatic brain tumors, chronic pain syndromes due to metastatic tumor, increased intracranial pressure, demyelinating diseases such as multiple sclerosis, inflammatory CNS diseases, such as subacute sclerosing panencephalitis, and other related neurological disorders and diseases.

SUMMARY OF THE INVENTION

The present invention provides a method for inhibiting the action of TNF for treating neurological conditions in a human by administering to the human therapeutically effective doses of a TNF antagonist selected from the group consisting of etanercept and infliximab, with or without the concurrent administration of therapeutically effective doses of methotrexate or Leflunomide, for reducing the inflammation of neuronal tissue of the human and/or preventing immune system damage to neuronal tissue. The TNF antagonist is administered subcutaneously, intravenously, intrathecally, or intramuscularly; methotrexate is administered orally or intramuscularly; and Leflunomide is administered orally.

DETAILED DESCRIPTION OF PREFERRED EMBODIMENT

TNF antagonist regimens to be used for neurological disorders are designed in two general ways: acute regimens, designed to achieve rapid blood levels and rapid action, wherein TNF blockade is desired for hours to days; and chronic regimens, where TNF blockade is desired for days, weeks, or months. Currently available TNF antagonists which are suitable for these regimens are etanercept (ENBREL™) from Immunex Corporation and infliximab (REMICADE™) from Centocor, Inc. Methotrexate or Leflunomide may be administered concurrently with the TNF antagonist for demyelinating diseases and certain other neurological disorders. Methotrexate and Leflunomide produce immune system modulation, which is shown to be beneficial in the treatment of demyelinating diseases and various autoimmune diseases. Additionally, methotrexate and Leflunomide have anti-tumor effects for certain malignancies. Lastly, methotrexate and Leflunomide have direct anti-inflammatory properties.

Trauma, injury, compression and other neurological disorders can affect individual nerves, nerve roots, the spinal cord, or the brain. The conditions which are of most concern here are the following:

1) acute spinal cord injury,
2) demyelinating diseases, such as multiple sclerosis,
3) herniated nucleus pulposus (herniated disc),
4) spinal cord compression due to metastatic cancer,
5) carpal tunnel syndrome (non-RA),
6) pituitary adenoma,
7) primary or metastatic brain tumors,
8) chronic pain syndromes due to metastatic tumor,
9) increased intracranial pressure, and
10) inflammatory CNS diseases, such as subacute sclerosing panencephalitis.

TNF antagonists are a novel way to treat neurologic trauma, injury, compression and neurological disorders in comparison with steroids. Experimental evidence has shown that excessive levels of TNF are released by injury to neuronal tissue. Accordingly, the use of TNF antagonists will result in amelioration of these neurological conditions. Because of the profoundly powerful action of the new TNF antagonists that have recently become available, these agents can prevent neurologic injury in a unique way, filling an urgent clinical need for more effective therapy. Also, because of the extremely safe side effect profile of these agents, they can be used either singly or in combination with other pharmacologic agents, such as methotrexate or Leflunomide. TNF antagonists can also safely be used with steroids, which are the only other class of agents which have been shown to be beneficial for certain of these conditions. Importantly, the TNF antagonists lack the adverse effects of steroids as previously described. Lastly, steroids are only partially effective or completely ineffective.

More detailed discussion of each of these clinical conditions is as follows:

1) Acute Spinal Cord Injury

About 10,000 cases occur per year in the U.S., with a current population of over 200,000 patients with residual neurologic damage, many of whom are paralyzed (quadriplegia or paraplegia). Current treatment for the acute injury is inadequate. In the early 1990's it was shown that early (within 8 hours of injury) treatment with high doses of steroids (methyl prednisolone) was beneficial for some of these patients. Surgical stabilization and spinal decompression is often necessary because of excessive swelling (edema) which can itself cause further severe injury to the cord due to further compression of the cord against its bony spinal canal. The etiology of most of these cases are motor vehicle accidents, with the remainder being sports injuries, falls, and other accidents. The window of opportunity for treatment is small, since massive swelling can occur within minutes.

The treatment regimen used here would be the acute regimen. This could involve any of the TNF antagonists, but currently etanercept would be the leading candidate. Etanercept is currently approved only for rheumatoid arthritis, and is used as a subcutaneous injection of 25 mg given twice a week.

This regimen produces peak blood levels in an average of 72 hours. A preferred method for acute spinal cord injury involves intravenous infusion to produce a serum concentration in the range of 0.5 mcg/ml to 50 mcg/ml, such concentrations are achieved more rapidly than can be produced by SC injection. This is a new method of dosing that is not being used for arthritis. This acute regimen is a unique delivery method for etanercept and is uniquely necessary for clinical neurologic conditions requiring rapid blockade of TNF.

2) Demyelinating Disease, Such As Multiple Sclerosis

Demyelinating neurological diseases, the most important being multiple sclerosis, are inadequately treated by currently available therapies, and continue to produce progressive, severe, neurologic impairment in a large population of patients in the United States and worldwide. There is experimental evidence which documents the role of TNF in multiple sclerosis. There is a wide body of work which documents the role of both cellular and humoral immunity in multiple sclerosis. Using the new TNF antagonists etanercept and infliximab, with or without concurrent use of methotrexate or Leflunomide, represents a novel approach to the treatment of these important disorders.

Several novel approaches are suggested. For acute demyelinating disease, it is paramount to use therapy which is rapidly effective to prevent permanent neurological damage. In this case, novel routes of administration of the TNF antagonists may be used. These novel routes include intrathecal administration of etanercept or infliximab; or intravenous administration of etanercept. Addition of methotrexate or Leflunomide concurrently with the use of the above TNF antagonists is another novel treatment which may be used for acute demyelinating disease. For other clinical forms of demyelinating disease, the more familiar routes of administration of etanercept (subcutaneous) or infliximab (intravenous) may be elected, with or without concurrent use of methotrexate or Leflunomide. These novel regimens are designed as such because of the complementary mechanisms of action and low toxicity of these biopharmaceutical agents.

3) Herniated Nucleus Pulposus (Herniated Disc)

Low back pain affects 70% of the population during their lifetime, with 25% of this group having pain in the sciatic distribution. Current pharmacologic treatment is inadequate, consisting of analgesics and anti-inflammatory medications (such as nonsteroidal anti-inflammatories (NSAIDS), such as ibuprofen (Motrin, etc.) and epidural steroid injections (generally regarded as having limited usefulness). Many of these patients eventually have surgery. Complications of lumbar disc herniation include permanent damage to the sciatic nerve, causing muscle weakness and atrophy in the lower extremity. Acute herniation with rapid onset of pain and sciatic nerve symptoms could be treated with the above acute regimen, with or without addition of the chronic regimen (described below), if symptoms continued. Treatment could also be reserved for patients not responding to conventional therapy. The acute treatment regimen, as outlined above, could be used for patients in whom rapid control of symptoms was desired. Most patients, however, would be treated conservatively and conventionally at first, with TNF blockade using one of the chronic regimens below added later for nonresponders. Herniated cervical discs would be treated the same way as herniated lumbar discs with the need for careful evaluation by a neurologist, neurosurgeon, and/or orthopedic surgeon for signs of neurologic compromise kept in mind. The chronic treatment regimen includes subcutaneous etanercept of 25 mg (dosage range 10 mg to 50 mg) once or twice a week; or infliximab administered by intravenous infusion once every two months (range once per month to once per six months).

4) Spinal Cord Compression Due to Metastatic Cancer

Cord compression due to metastatic cancer is a catastrophic event leading to rapid paralysis if not quickly diagnosed and treated. It is most common with cancers of the breast, colon, lung and prostate, but can be a complication of metastatic disease from a wide variety of malignancies, including melanoma and multiple myeloma. Current treatment regimens include high dose steroids, emergency radiation treatment, and/or emergent surgical decompression. Paralysis can occur within hours, so treatment must be initiated within this time period to avoid permanent sequelae. The mechanism of action of TNF blockage here would be similar to that above. In addition, it is possible that TNF blockade could be directly tumoricidal or tumoristatic with certain malignancies. Impending cord compression could be treated with the chronic regimen. However, as explained above, most patients would need to be emergently treated with the acute regimen, as outlined above.

5) Carpal Tunnel Syndrome (CTS) (non-RA)

Carpal tunnel syndrome involves compression of the median nerve at the wrist, causing pain and neurologic symptoms in the hand. It is a common condition, being aggravated by repetitive stress injury (RSI) in the workplace (such as typists and writers, manual laborers, etc.), and is also a complication of rheumatoid arthritis (RA). Use of TNF blockade for carpal tunnel syndrome in patients with established RA would likely be covered by the existing arthritis medication for treating RA. But most patients with carpal tunnel syndrome do not have RA; they either have idiopathic CTS or CTS caused by RSI. CTS is a major cause of disability and responds poorly to current treatment regimens, which include NSAIDS, wrist splinting, and injection of steroids. The chronic treatment regimen as outlined above would be used for the treatment of CTS (non-RA type).

6) Pituitary Adenoma

Benign pituitary tumors grow adjacent to the optic chiasm. Unrestrained growth causes compression of the optic nerve, causing visual field defects and eventuating in blindness. Treatments include radiation, surgical decompression and bromocriptine. TNF blockade could prove to be a valuable adjunctive therapy, and could be either the acute or chronic treatment regimen, depending on the clinical picture.

7) Primary or Metastatic Brain Tumors

Primary brain tumors can be either benign (most commonly meningioma) or malignant (usually gliomas). Metastatic brain tumors can be from any source, most commonly lung cancer, breast cancer, or other malignancies such as melanoma. Treatment for these tumors is primarily surgery or radiation, with generally poor response to chemotherapy. Many of these tumors cause surrounding edema which can cause further neurologic deterioration. TNF blockade, either the acute or chronic treatment regimen, could be beneficial while these patients are awaiting surgery. Additionally, TNF blockade, as discussed above, could have direct tumor inhibiting properties.

In an alternate treatment regimen, methotrexate orally or intramuscularly, may be administered concurrently with a TNF antagonist, wherein the dosage level of methotrexate is in the range of 2.5 mg to 25 mg, given from once weekly to once monthly. If the dose is given orally, the total weekly dose may be given in three equal parts over 36 hours, with 12 hours between each dose. The preferred dosage range is 7.5 mg to 15 mg administered weekly.

As another alternate treatment, instead of administering methotrexate, Leflunomide may be administered orally concurrently with a TNF antagonist, wherein the dosage level of Leflunomide is in the range of 10 mg to 100 mg per day for the first 3 days, and 5 mg to 20 mg daily thereafter.

8) Chronic Pain Syndromes Due to Metastatic Tumor

Pain due to metastatic cancer is inadequately treated by currently used agents. It is probable that the mechanism of action of this pain is mediated in part by the overproduction of TNF. TNF blockade could be beneficial for selected tumors, particularly bone metastases where compression is involved. The chronic treatment regimens would be used. One general note of caution when treating malignancies is necessary: While TNF blockade is likely to have an antitumor effect with certain malignancies, it is also possible that TNF blockade could increase growth rates with certain malignancies.

In an alternate treatment regimen, methotrexate orally or intramuscularly, may be administered concurrently with a TNF antagonist, wherein the dosage level of methotrexate is in the range of 2.5 mg to 25 mg, given from once weekly to once monthly.

As another alternate treatment, instead of administering methotrexate, Leflunomide may be administered orally concurrently with a TNF antagonist, wherein the dosage level of Leflunomide is in the range of 10 mg to 100 mg per day for the first 3 days, and 5 mg to 20 mg daily thereafter.

9) Elevated Intracranial Pressure (EICP)

EICP can be idiopathic (Pseudotumor cerebri) or caused by certain drugs (vitamin A excess, isotretinoin, tetracyclines, etc.) caused by malignancy (as above), or by benign tumors (e.g. cystercircosis) TNF blockade, either the acute or chronic treatment regimen, could be helpful.

OPERATION OF THE PRESENT INVENTION

1) Chronic Regimen Dosing with Etanercept

For adults the dose is 25 mg subcutaneously (range 10 mg to 50 mg) administered in a range of twice a week to once a month. The initial regimen being 25 mg subcutaneously twice a week and for children 0.4 mg/kg given twice a week. Expected serum concentrations with this regimen would be about 3.0 mcg/ml, with a desired range between 0.5 and 10 mcg/ml. Other routes for chronic administration could include IM or IV dosing regimens.

In an alternate treatment regimen, methotrexate orally or intramuscularly, may be administered concurrently with etanercept, wherein the dosage level of methotrexate is in the range of 2.5 mg to 25 mg, given from once weekly to once monthly.

As another alternate treatment, instead of administering methotrexate, Leflunomide may be administered orally concurrently with a TNF antagonist, wherein the dosage level of Leflunomide is in the range of 10 mg to 100 mg per day for the first 3 days, and 5 mg to 20 mg daily thereafter.

2) Acute Regimen Dosing with Etanercept

Acute treatment regimens include administration of etanercept by SC, IM, IV and intrathecal dosing routes for acute administration.

In an alternate treatment, methotrexate may be administered concurrently, orally or intramuscularly, wherein the dosage level is in the range of 2.5 mg to 25 mg, given from once weekly to once monthly. The concurrent treatment with methotrexate may be added to any of these acute treatment regimens with etanercept.

As another alternate treatment, instead of administering methotrexate, Leflunomide may be administered orally concurrently with a TNF antagonist, wherein the dosage level of Leflunomide is in the range of 10 mg to 100 mg per day for the first 3 days, and 5 mg to 20 mg daily thereafter. The concurrent treatment with Leflunomide may be added to any of these acute treatment regimens with etanercept.

2A) Acute IV Regimen with Etanercept

Etanercept is administered by IV infusion in a quantity sufficient to produce a serum concentration in the range of 0.5 mcg/ml to 50 mcg/ml.

2B) Acute IM Regimen for Etanercept

Etanercept is given by intramuscular administration in a dose of 50 mg having a range of 25 mg to 100 mg.

2C) Acute Intrathecal Regimen with Etanercept

There may be clinical use for etanercept in the cerebrospinal fluid, such as for treatment of CNS lesions (demyelinating diseases, brain tumors, cord compression). Intrathecal therapy means introducing the TNF antagonist into the cerebrospinal fluid of the patient. The exact dosage is on the order of 10 mg (range 1 mg to 50 mg).

3) Chronic Treatment Regimen with Infliximab

Chronic indications for infliximab include herniated nucleus pulposus (herniated disk), carpal tunnel syndrome, pituitary adenoma, demyelinating disease, primary or metastatic brain tumors and chronic pain syndromes due to metastatic tumor.

Usual dosage for infliximab is 5 mg/kg given by IV infusion every two months with a range of 2.5 mg/kg to 20 mg/kg given every 2 weeks to 2 months.

In an alternate treatment regimen, methotrexate orally or Intramuscularly, may be administered concurrently with infliximab, wherein the dosage level of methotrexate is in the range of 2.5 mg to 25 mg, given from once weekly to once monthly.

As another alternate treatment, instead of administering methotrexate, Leflunomide may be administered orally concurrently with a TNF antagonist, wherein the dosage level of Leflunomide is in the range of 10 mg to 100 mg per day for the first 3 days, and 5 mg to 20 mg daily thereafter.

4) Acute Treatment Regimen with Infliximab

Acute indications for infliximab include acute spinal cord injury, acute demyelinating disease, spinal cord compression and increased intracranial pressure.

The dosage for infliximab used for the acute regimen is 10 mg/kg administered by IV infusion once (range 2.5 mg/kg to 25 mg/kg). The dose for the intrathecal administration of infliximab is 0.3 mg/kg having a range of 0.1 mg/kg to 1 mg/kg.

In an alternate treatment, methotrexate may be administered concurrently, orally or intramuscularly, wherein the dosage level is in the range of 2.5 mg to 25 mg, given from once weekly to once monthly. The concurrent treatment with methotrexate may be added to any of these acute treatment regimens with infliximab.

As another alternate treatment, instead of administering methotrexate, Leflunomide may be administered orally concurrently with a TNF antagonist, wherein the dosage level of Leflunomide is in the range of 10 mg to 100 mg per day for The first 3 days, and 5 mg to 20 mg daily thereafter. The concurrent treatment with Leflunomide may be added to any of these acute treatment regimens with infliximab.

5) Treatment with Existing Regimens

The treatment regimens of the present invention may be used in conjunction with or in place of existing treatments, such as steroids and surgery. When the treatment regimens of the present invention are used concurrently with currently available treatments, the results are additive and therefore beneficial.

ADVANTAGES OF THE PRESENT INVENTION

Accordingly, an advantage of the present invention is that it provides a TNF antagonist, with or without the concurrent administration of methotrexate or Leflunomide, for a new pharmacologic treatment of neurological disorders, trauma, injuries and compression affecting the nervous system of the human body, or demyelinating neurologic disease, such that the use of these TNF antagonists will result in the amelioration of these neurological conditions.

Another advantage of the present invention is that it provides for a TNF antagonist, with or without the concurrent administration of methotrexate or Leflunomide, for providing suppression and inhibition of the action of TNF in a human to treat neurological injury, trauma or compression, or demyelinating neurologic disease, or inflammatory disease of the nervous system.

Another advantage of the present invention is that it provides a TNF antagonist, with or without the concurrent administration of methotrexate or Leflunomide, that reduces and prevents further neurological inflammation to the patient by inhibiting the action of TNF in the human body for the immediate, short term (acute conditions) and long term (chronic conditions), such that this reduction and prevention of inflammation will produce clinical improvement in the patient and will give the patient a better opportunity to heal, slows disease progression, prevents neurological damage, or otherwise improves the patient's health.

Another advantage of the present invention is that it provides for a TNF antagonist, with or without the concurrent administration of methotrexate or Leflunomide, that can offer acute and chronic treatment regimens for neurological conditions caused by neurological trauma, compression, injury and/or disease, such conditions including acute spinal cord injury, herniated nucleus pulposus (herniated disc), spinal cord compression due to metastatic cancer, carpal tunnel syndrome (non-RA), demyelinating disease, pituitary adenoma, primary or metastatic brain tumors, chronic pain syndromes due to metastatic tumor, increased intracranial pressure, and other related neurological disorders and diseases.

Another advantage of the present invention is to provide a TNF antagonist, with or without the concurrent administration of methotrexate or Leflunomide, to treat neurologic disorders in humans either acutely or chronically by blocking the action of TNF and thereby modulating the immune response affecting neuronal tissue.

A latitude of modification, change, and substitution is intended in the foregoing disclosure, and in some instances, some features of the invention will be employed without a corresponding use of other features. Accordingly, it is appropriate that the appended claims be construed broadly and in a manner consistent with the spirit and scope of the invention herein.

What is claimed is:

[1. A method for inhibiting the action of TNF for treating neurological conditions in a human by administering a TNF antagonist for reducing the inflammation of neuronal tissue of said human, or for modulating the immune response affecting neuronal tissue of said human, comprising the step of:

a) administering a therapeutically effective dosage level to said human of said TNF antagonist selected from the group consisting of etanercept and infliximab for reducing the inflammation of neuronal tissue of said human, or for modulating the immune response affecting neuronal tissue of said human.]

[2. A method for inhibiting the action of TNF in accordance with claim 1, wherein the step of administering said TNF antagonist is performed subcutaneously, intravenously, intrathecally, or intramuscularly.]

[3. A method for inhibiting the action of TNF in accordance with claim 1, wherein the step of administering said dosage level is for treating neurological diseases and disorders.]

[4. A method for inhibiting the action of TNF in accordance with claim 1, wherein the step of administering said dosage level is for treating neurological traumas and injuries.]

[5. A method for inhibiting the action of TNF in accordance with claim 1, wherein the step of administering said dosage level is for treating acute spinal cord injury.]

[6. A method for inhibiting the action of TNF in accordance with claim 1, wherein the step of administering said dosage level is for treating herniated discs.]

[7. A method for inhibiting the action of TNF in accordance with claim 1, wherein the step of administering said dosage level is for treating spinal cord compression.]

[8. A method for inhibiting the action of TNF in accordance with claim 1, wherein the step of administering said dosage level is for treating carpal tunnel syndrome (non-RA type).]

[9. A method for inhibiting the action of TNF in accordance with claim 1, wherein the step of administering said dosage level is for treating pituitary adenoma.]

[10. A method for inhibiting the action of TNF in accordance with claim 1, wherein the step of administering said dosage level is for treating primary or metastatic brain tumors.]

[11. A method for inhibiting the action of TNF in accordance with claim 1, wherein the step of administering said dosage level is for treating chronic pain syndrome due to metastatic tumor.]

[12. A method for inhibiting the action of TNF in accordance with claim 1, wherein the step of administering said dosage level is for treating increased intracranial pressure.]

[13. A method for inhibiting the action of TNF in accordance with claim 1, wherein the step of administering said dosage level is for treating central nervous system lesions.]

[14. A method for inhibiting the action of TNF in accordance with claim 1, wherein the step of administering said dosage level is for treating autoimmune neurological diseases.]

[15. A method for inhibiting the action of TNF in accordance with claim 1, wherein the step of administering said dosage level is for treating multiple sclerosis.]

[16. A method for inhibiting the action of TNF in accordance with claim 1, wherein the step of administering said dosage level is for treating subacute sclerosing panencephalitis.]

[17. A method for inhibiting the action of TNF in accordance with claim 1, wherein the step of administering said etanercept is performed subcutaneously in said human wherein said dosage level is in the range of 10 mg to 50 mg for acute or chronic regimens.]

[18. A method for inhibiting the action of TNF in accordance with claim 1, wherein the step of administering said etanercept is performed subcutaneously in said human wherein said dosage level is 25 mg for acute or chronic regimens.]

[19. A method for inhibiting the action of TNF in accordance with claim 1, wherein the step of administering said etanercept is performed intramuscularly in said human wherein said dosage level is in the range of 25 mg to 100 mg.]

[20. A method for inhibiting the action of TNF in accordance with claim 1, wherein the step of administering said etanercept is performed intravenously in said human wherein said dosage level produces a serum concentration in the range of 0.5 mcg/Ml to 50 mcg/ml.]

[21. A method for inhibiting the action of TNF in accordance with claim 1, wherein the step of administering said etanercept is performed intravenously by infusion in said human wherein said dosage level produces a serum concentration of 10 mcg/ml.]

[22. A method for inhibiting the action of TNF in accordance with claim 1, wherein the step of administering said etanercept is performed intrathecally in said human wherein said dosage level is in the range of 1 mg to 50 mg.]

[23. A method for inhibiting the action of TNF in accordance with claim 1, wherein the step of administering said infliximab is performed subcutaneously in said human wherein said dosage level is in the range of 0.1 mg/kg to 2.5 mg/kg.]

[24. A method for inhibiting the action of TNF in accordance with claim 1, wherein the step of administering said infliximab is performed intramuscularly in said human wherein said dosage level is in the range of 0.1 mg/kg to 2.5 mg/kg for acute or chronic regimens.]

[25. A method for inhibiting the action of TNF in accordance with claim 1, wherein the step of administering said infliximab is performed intravenously in said human wherein said dosage level is in the range of 2.5 mg/kg to 20 mg/kg.]

[26. A method for inhibiting the action of TNF in accordance with claim 1, wherein the step of administering said infliximab is performed intrathecally in said human wherein said dosage level is in the range of 0.05 mg/kg to 1 mg/kg.]

[27. A method for inhibiting the action of TNF for treating neurological conditions in a human by administering a TNF antagonist for reducing the inflammation of neuronal tissue of said human, or for modulating the immune response affecting neuronal tissue of said human, comprising the steps of:

a) administering a therapeutically effective dosage level to said human of said TNF antagonist selected from the group consisting of etanercept and infliximab for reducing the inflammation of neuronal tissue of said human, or for modulating the immune response affecting neuronal tissue of said human; and b) administering a therapeutically effective dosage level to said human of methotrexate or Leflunomide for reducing the inflammation of neuronal tissue of said human, or for modulating the immune response affecting neuronal tissue of said human.]

[28. A method for inhibiting the action of TNF in accordance with claim 27, wherein the steps of administering are performed subcutaneously, intravenously, intrathecally, orally or intramuscularly.]

[29. A method for inhibiting the action of TNF in accordance with claim 27, wherein the steps of administering said dosage levels are for treating neurological diseases and disorders.]

[30. A method for inhibiting the action of TNF in accordance with claim 27, wherein the steps of administering said dosage levels are for treating primary or metastatic brain tumors.]

[31. A method for inhibiting the action of TNF in accordance with claim 27, wherein the steps of administering said dosage levels are for treating chronic pain syndrome due to metastatic tumor.]

[32. A method for inhibiting the action of TNF in accordance with claim 27, wherein the steps of administering said dosage levels are for treating central nervous system lesions.]

[33. A method for inhibiting the action of TNF in accordance with claim 27, wherein the steps of administering said dosage levels are for treating autoimmune neurological diseases.]

[34. A method for inhibiting the action of TNF in accordance with claim 27, wherein the steps of administering said dosage levels are for treating multiple sclerosis.]

[35. A method for inhibiting the action of TNF in accordance with claim 27, wherein the steps of administering said dosage levels are for treating subacute sclerosing, panencephalitis.]

[36. A method for inhibiting the action of TNF in accordance with claim 27, wherein the step of administering said etanercept is performed subcutaneously in said human wherein said dosage level is in the range of 10 mg to 50 mg for acute or chronic regimens.]

[37. A method for inhibiting the action of TNF in accordance with claim 27, wherein the step of administering said etanercept is performed subcutaneously in said human wherein said dosage level is 25 mg for acute or chronic regimens.]

[38. A method for inhibiting the action of TNF in accordance with claim 27, wherein the step of administering said etanercept is performed intramuscularly in said human wherein said dosage level is in the range of 25 mg to 100 mg.]

[39. A method for inhibiting the action of TNF in accordance with claim 27, wherein the step of administering said etanercept is performed intravenously in said human wherein said dosage level produces a serum concentration in the range of 0.5 mcg/ml to 50 mcg/ml.]

[40. A method for inhibiting the action of TNF in accordance with claim 27, wherein the step of administering said etanercept is performed intravenously by infusion in said human wherein said dosage level produces a serum concentration of 10 mcg/ml.]

[41. A method for inhibiting the action of TNF in accordance with claim 27, wherein the step of administering said etanercept is performed intrathecally in said human wherein said dosage level is in the range of 1 mg to 50 mg.]

[42. A method for inhibiting the action of TNF in accordance with claim 27, wherein the step of administering said infliximab is performed subcutaneously in said human wherein said dosage level is in the range of 0.1 mg/kg to 2.5 mg/kg.]

[43. A method for inhibiting the action of TNF in accordance with claim 27, wherein the step of administering said infliximab is performed intramuscularly in said human wherein said dosage level is in the range of 0.1 mg/1 kg to 2.5 mg/kg for acute or chronic regimens.]

[44. A method for inhibiting the action of TNF in accordance with claim 27, wherein the step of administering said infliximab is performed intravenously in said human wherein said dosage level is in the range of 2.5 mg/kg to 20 mg/kg.]

[45. A method for inhibiting the action of TNF in accordance with claim 27, wherein the step of administering said infliximab is performed intrathecally in said human wherein said dosage level is in the range of 0.05 mg/kg to 1 mg/kg.]

[46. A method for inhibiting the action of TNF in accordance with claim 27, wherein the step of administering said methotrexate is performed orally or intramuscularly in said human wherein said dosage level is in the range of 2.5 mg to 25 mg given from once weekly to once monthly.]

[47. A method for inhibiting the action of TNF in accordance with claim 27, wherein the step of administering said Leflunomide is performed orally in said human wherein said dosage level is in the range of 10 mg to 100 mg per day for the first 3 days, and 5 mg to 20 mg per day thereafter.]

*48. A method for inhibiting the action of TNF for treating neurological conditions in a human by administering a TNF antagonist for reducing the inflammation of neuronal tissue of said human, or for modulating the immune response affecting neuronal tissue of said human, comprising the step of:*

*a) administering a therapeutically effective dosage level to said human of said TNF antagonist which is etanercept, for reducing the inflammation of neuronal tissue of said human, or for modulating the immune response affecting neuronal tissue of said human, and*

*b) the step of administering said TNF antagonist is performed intrathecally in said human wherein said dosage level is in the range of 1 mg to 50 mg.*

*49. A method for inhibiting the action of TNF in accordance with claim 48, wherein the step of administering said dosage level is for treating herniated discs.*

*50. A method for inhibiting the action of TNF in accordance with claim 48, wherein the step of administering said dosage level is for treating spinal cord compression.*

* * * * *